(12) United States Patent
Barrelle

(10) Patent No.: US 7,682,344 B2
(45) Date of Patent: Mar. 23, 2010

(54) DEVICE FOR PROTECTING AN INJECTION APPARATUS

(75) Inventor: Laurent Barrelle, Saint Nizier du Moucherotte (FR)

(73) Assignee: Becton Dickinson France S.A.S., Pont de Claix (FR)

( * ) Notice: Subject to any disclaimer, the term of this patent is extended or adjusted under 35 U.S.C. 154(b) by 352 days.

(21) Appl. No.: 10/573,225

(22) PCT Filed: Sep. 10, 2004

(86) PCT No.: PCT/FR2004/002306

§ 371 (c)(1),
(2), (4) Date: Apr. 23, 2008

(87) PCT Pub. No.: WO2005/030301

PCT Pub. Date: Apr. 7, 2005

(65) Prior Publication Data

US 2008/0208140 A1 Aug. 28, 2008

(30) Foreign Application Priority Data

Sep. 26, 2003 (FR) .................................. 03 11313

(51) Int. Cl.
*A61M 5/32* (2006.01)
(52) U.S. Cl. ...................................... 604/198; 604/192
(58) Field of Classification Search ................. 604/192, 604/197, 198, 110
See application file for complete search history.

(56) References Cited

U.S. PATENT DOCUMENTS

| 5,591,138 | A | * | 1/1997 | Vaillancourt | ................. 604/263 |
| 6,110,147 | A | * | 8/2000 | Perouse | ...................... 604/198 |
| 2002/0156426 | A1 | * | 10/2002 | Gagnieux et al. | ........... 604/197 |
| 2003/0212380 | A1 | | 11/2003 | Barrelle | |

FOREIGN PATENT DOCUMENTS

| EP | 0966983 | 12/1999 |
| FR | 2830765 | 4/2003 |
| FR | 2835753 | 8/2003 |

* cited by examiner

*Primary Examiner*—Kevin C Sirmons
*Assistant Examiner*—Maria E Doukas
(74) *Attorney, Agent, or Firm*—David M. Fortunato; Cohen Pontani Lieberman & Pavane LLP

(57) ABSTRACT

A device for protecting an injection apparatus for injecting a product, the said apparatus comprising a needle and a piston connected to an actuating rod surmounted by a piston head, the said device comprising: a support sleeve, a protective sleeve for protecting the needle, first retaining means for holding the protective sleeve in its standby configuration in a first position, second retaining means for holding the protective sleeve in its standby configuration in a second position, an intermediate collar comprising collaboration means for collaborating with the piston head, and deactivation means for deactivating the first and second retaining means. The second retaining means being able to be deactivated by the deactivation means of the intermediate collar by the release of the pressure of the piston head on the collaboration means of the intermediate collar to allow the protective sleeve to deploy under the action of pushing means.

6 Claims, 5 Drawing Sheets

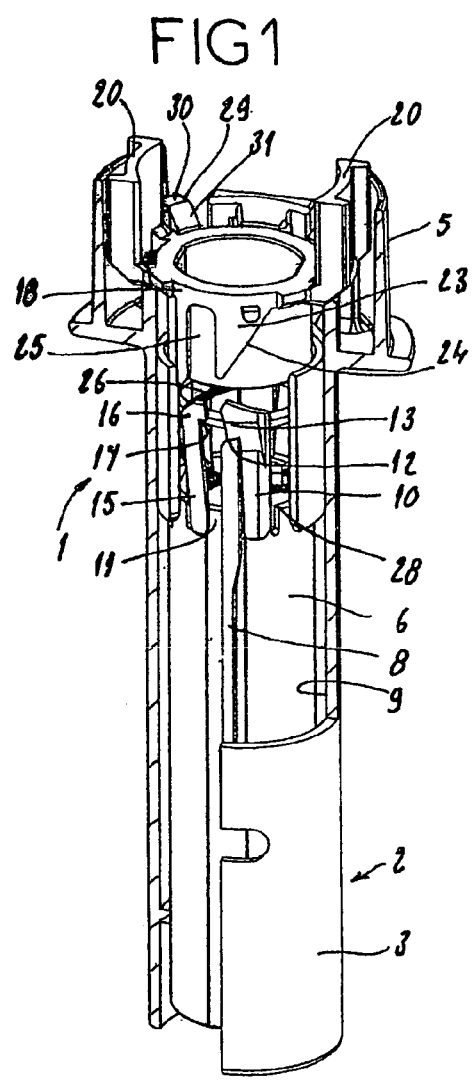
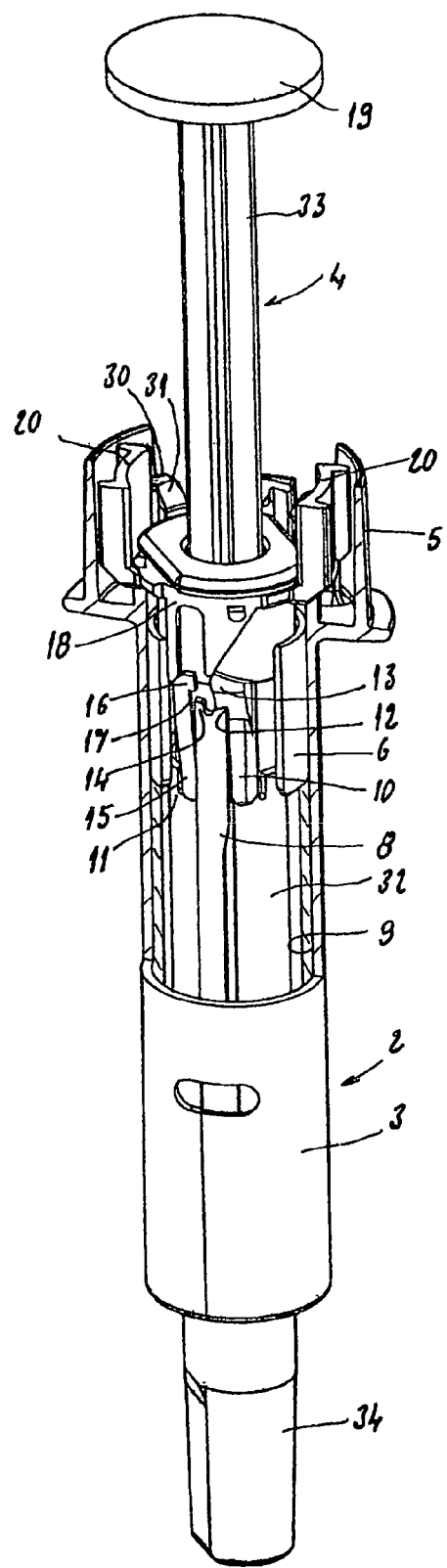

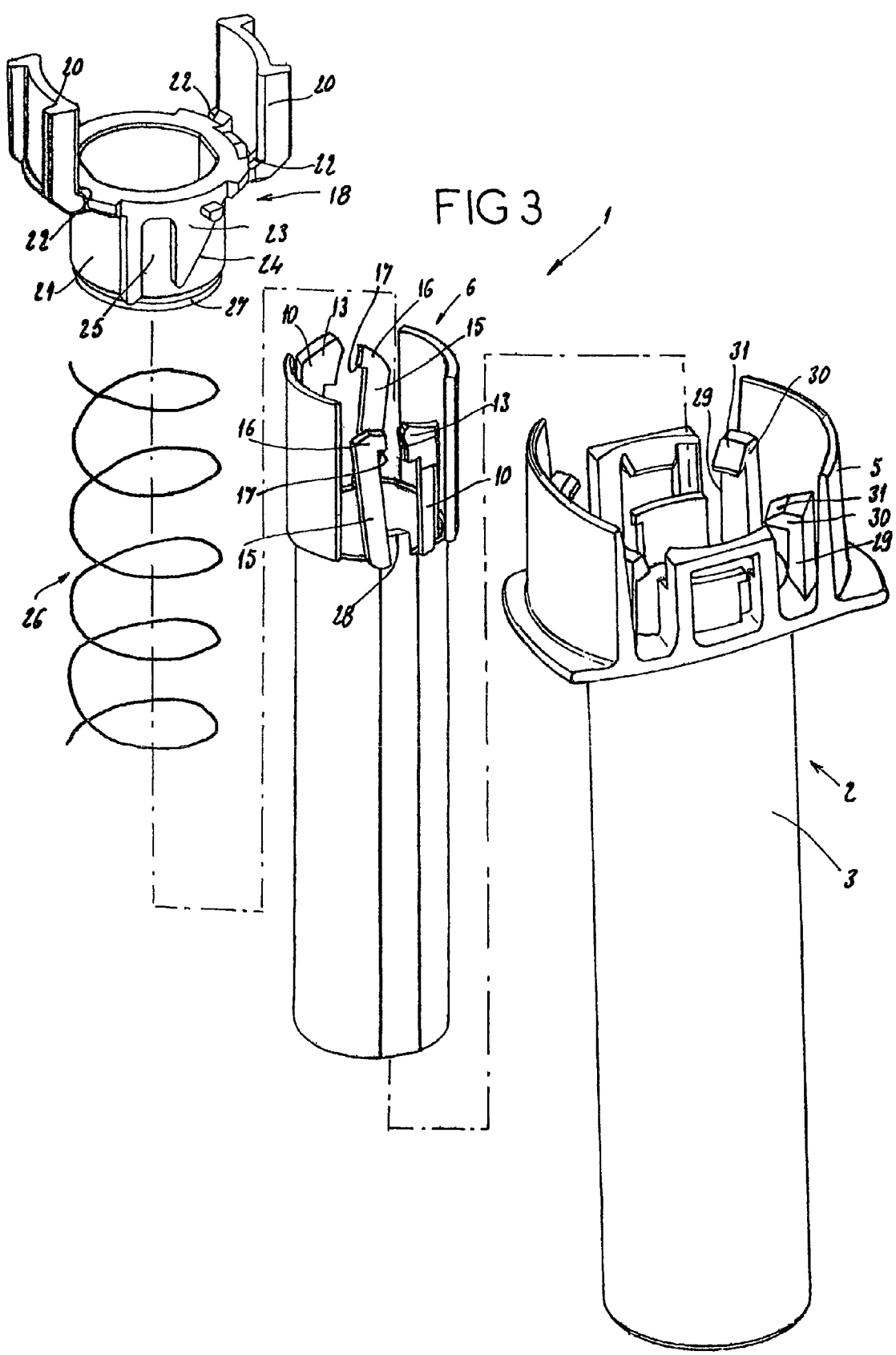

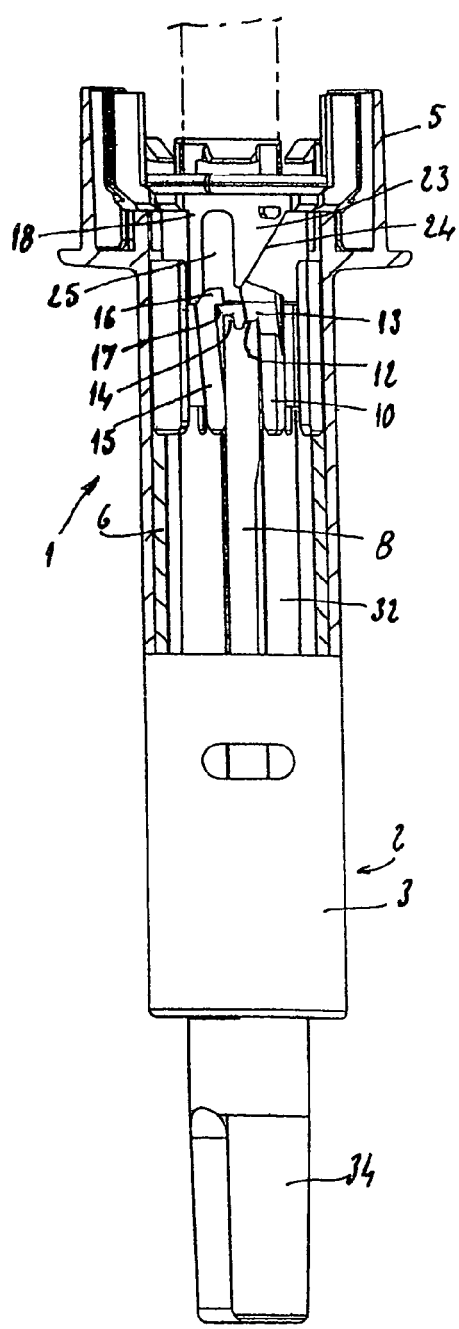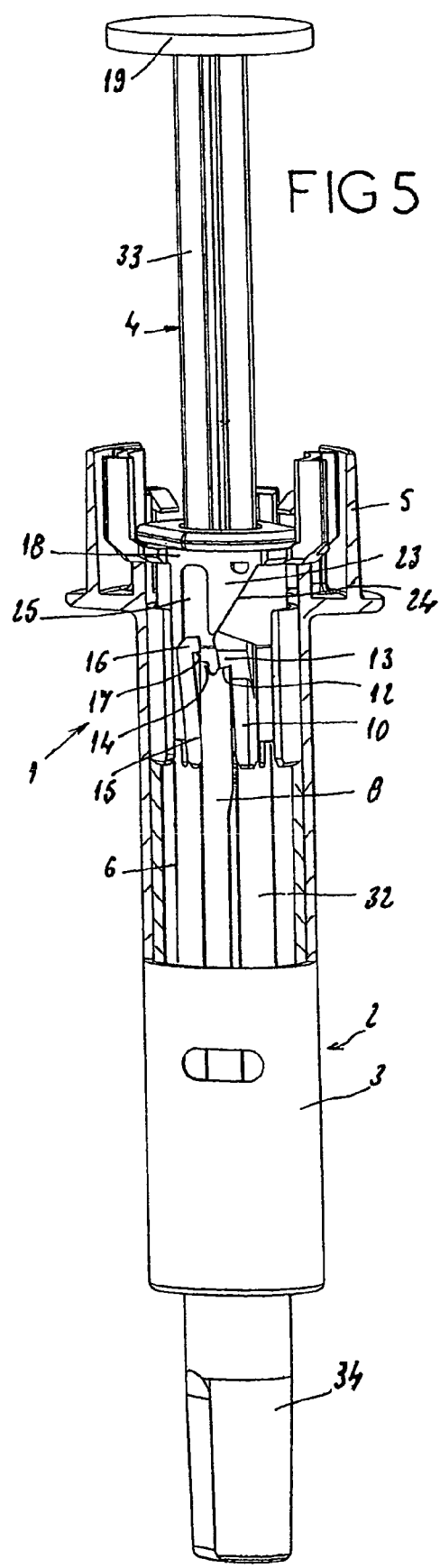

FIG 6
FIG 7
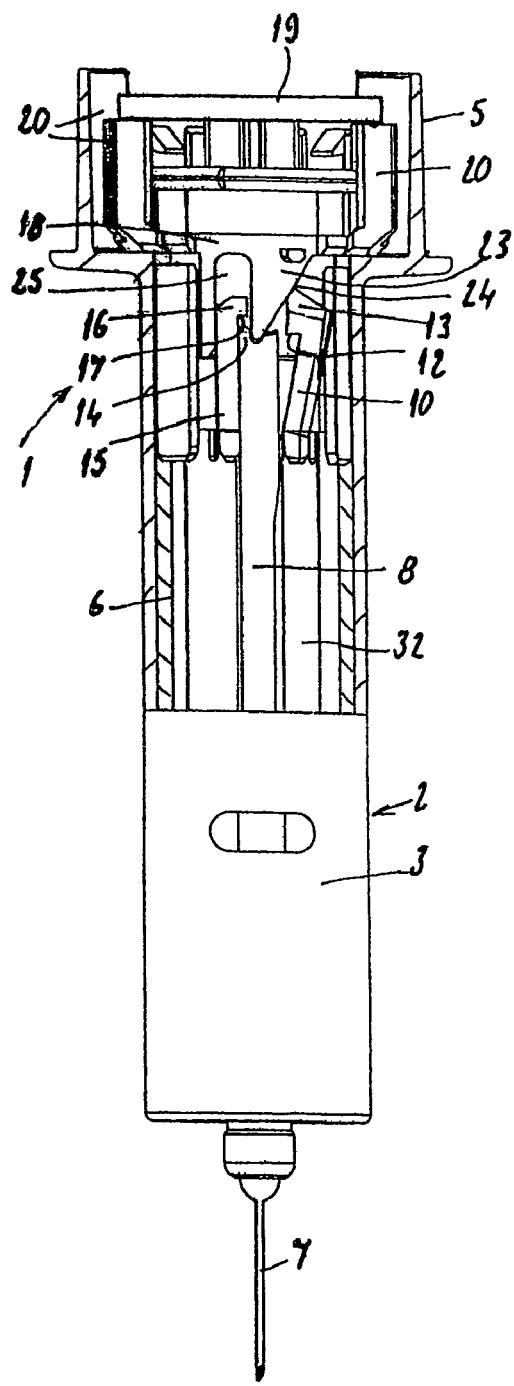
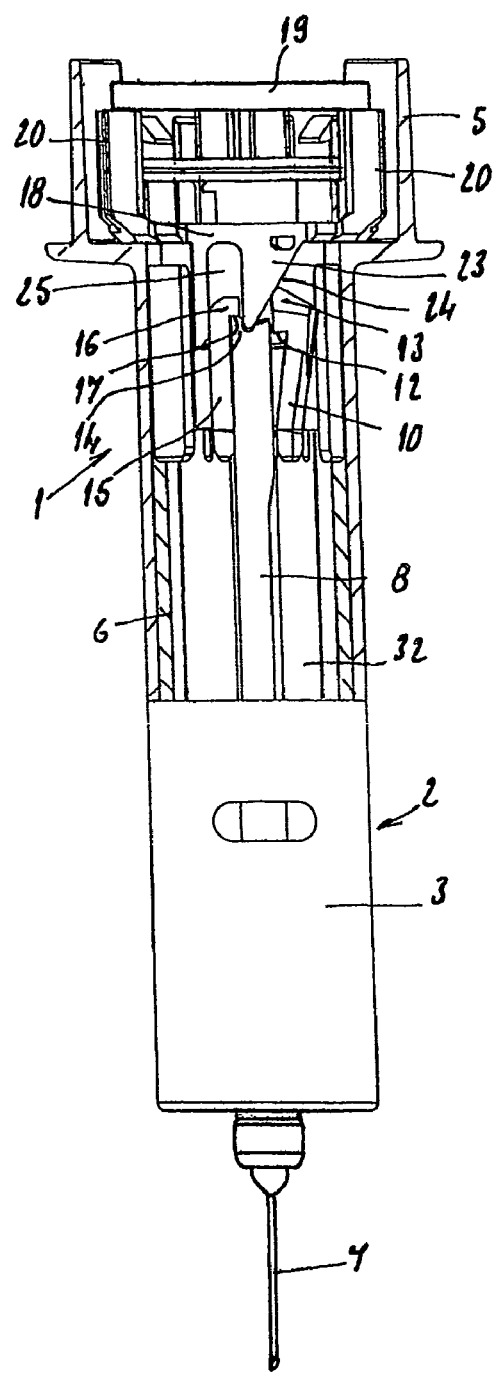

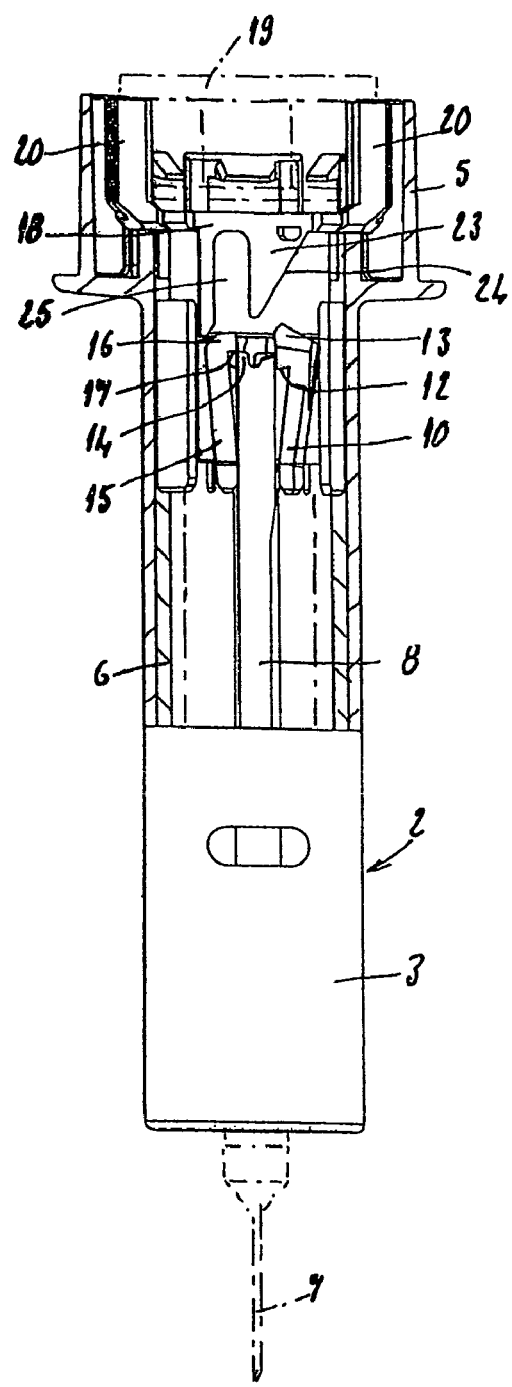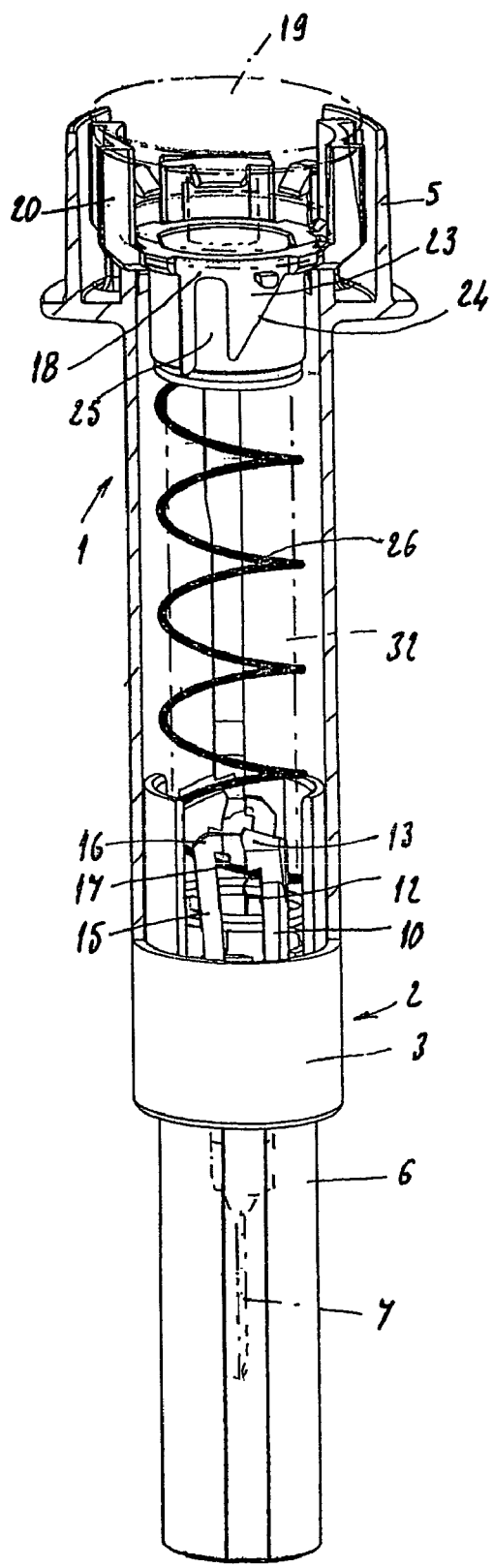

DEVICE FOR PROTECTING AN INJECTION APPARATUS

PRIORITY CLAIM

This is a U.S. national stage of application No. PCT/FR04/02306, filed on Sept. 10, 2004, which claims Priority to French Application No.: 0311313, filed: Sept. 26, 2003; the contents of both being incorporated herein by reference.

1. FIELD Of THE INVENTION

The present invention relates to a protective device for protecting apparatuses for injecting a product, particularly for medical use, such a syringes.

In the description which follows the terms "proximal" and "distal" are considered with respect to the direction in which the product is injected.

2. DISCUSSION OF RELATED ART

Product injection apparatuses such as syringes are well known. Prefilled syringes are usually filled with a drug before being distributed to the end-user.

However, the end-user is constantly exposed to the risks of needle-stick injuries which are liable to occur after injection.

In order to minimize these risks, it is known practice for syringes to be equipped with a protective device in the form of a sleeve that slides with respect to the syringe and is supposed to cover the needle after injection.

Some of these devices need to be fitted manually by the end-user and are therefore rather unreliable. Other protective devices are activated by a spring upon the action of the end-user. In this case also, the triggering of the protective device depends on an action on the part of the end-user and is therefore haphazard.

To overcome these disadvantages there are protective devices that are activated automatically by a spring at the end of injection. One of the problems encountered with these devices is the risk of activating them prematurely or inadvertently, particularly while they are being manufactured and/or assembled with syringes.

SUMMARY OF THE INVENTION

There is therefore a need for a device for protecting a syringe that can be activated automatically but only at the end of injection or only when the end-user so decides.

The objective of the invention is therefore to provide a device for protecting an injection apparatus, particularly a syringe, activated automatically at the end of injection but unable to be activated inadvertently, thus ensuring perfect safety against the risk of needle-stick injuries.

The present invention relates to a device for protecting an injection apparatus for injecting a product, particularly a syringe, the said apparatus comprising a reservoir fitted with a needle at its distal end and a piston connected to an actuating rod surmounted by a piston head, the said device comprising:

a support sleeve comprising a body able to accommodate the injection apparatus and a proximal end part, a protective sleeve able to slide with respect to the support sleeve between a retracted standby configuration in which the needle is exposed and a deployed protective configuration in which it covers the needle, the said device being characterized in that it comprises:

first retaining means for holding the protective sleeve in its standby configuration in a first position, known as the injection position, second retaining means for holding the protective sleeve in its standby configuration in a second position, known as the end-of-injection position, which is appreciably offset in the distal direction with respect to the support sleeve, an intermediate collar situated in the proximal end part of the support sleeve, able to slide with respect to this support sleeve within the said proximal end part, the said collar comprising means of collaboration with the piston head of the injection apparatus, and means of deactivating the said first and second retaining means, the said first retaining means being able to be deactivated by the said deactivation means of the said intermediate collar by pressure of the piston head in the distal direction on the said means of collaboration of the said intermediate collar so as to cause the protective sleeve to slide in its retracted standby configuration between the said first injection position and the said second end-of-injection position, and the said second retaining means being able to be deactivated by the deactivation means of the said intermediate collar by release of the pressure of the piston head on the said collaboration means of the said intermediate collar so as to allow the protective sleeve to deploy under the action of pushing means.

Advantageously, the means of collaboration of the intermediate collar with the piston head comprise two diametrically opposed legs running in the proximal direction, slightly offset from the body of the collar in the radial direction and connected to the proximal end of the collar by radial bridges.

Advantageously, the first retaining means comprise two diametrically opposed longitudinal bulges formed on the internal surface of the wall of the body of the support sleeve, each bulge at its proximal end comprising an internal retaining ramp and two first tabs running axially in the proximal direction from the proximal end of the protective sleeve, each of the said first tabs being provided at its proximal end with a projection the distal face of which is inclined and able to rest on the internal ramp of the proximal end of one said bulge. Thus, the collaboration of the internal ramp of each bulge and of the distal surface of the projection of the first tab facing the bulge holds the protective sleeve in its first, injection, position in its retracted standby configuration.

Advantageously, the second retaining means comprise a transverse retaining surface situated at the proximal end of each bulge facing the internal ramp of the said bulge and two second tabs running in the proximal direction from the proximal end of the protective sleeve along an axis slightly inclined with respect to the longitudinal axis of the injection apparatus, each second tab being situated facing one said first tab, each second tab being equipped at its proximal end with a hooked portion the proximal face of which is able to rest against the transverse retaining surface of the bulge facing it. Thus, the collaboration of the transverse surface of the proximal end of the bulge and of the proximal surface of the hooked portion of the second tab holds the protective sleeve in its second, end-of-injection, position in its retracted standby configuration.

Advantageously, the deactivation means for deactivating the first and second retaining means are in the form of a surface projecting radially from the body of the collar, the said surface being able to collaborate with the said first tabs and with the said second tabs to deflect them circumferentially.

Advantageously, the pushing means are in the form of a spring the proximal end of which bears against the distal end of the intermediate collar and the distal end of which bears against an annular rim formed on the internal surface of the protective sleeve at its proximal end.

BRIEF DESCRIPTION OF THE DRAWINGS

The attached figures illustrate, by way of example, one preferred embodiment of the device according to the invention.

FIG. 1 is perspective view thereof;

FIG. 2 is a perspective view thereof with the syringe assembled;

FIG. 3 is an exploded perspective view showing the elements of the device according to the invention;

FIGS. 4 and 5 are side views of the device according to the invention in its retracted standby configuration in its first, injection, position, before and after assembly of the syringe, respectively;

FIG. 6 is a side view of the device of the invention while the first retaining means are in the process of being deactivated;

FIG. 7 is a side view of the device according to the invention in its retracted standby configuration in its second, end-of-injection, position;

FIG. 8 is a side view of the device according to the invention while the second retaining means are in the process of being deactivated;

FIG. 9 is a side view of the device according to the invention in its deployed protective configuration.

DETAILED DESCRIPTION OF THE DRAWINGS

FIGS. 1 to 3 depict a device 1 for protecting an injection apparatus. This device 1 comprises a support sleeve 2 comprising a body 3 able to accommodate an injection apparatus 4 such as the syringe shown in FIG. 2 comprising a reservoir 32, a rod 33 for actuating a piston, a piston head 19 and a cap 34 covering a needle (see FIG. 6). The support sleeve 2 also comprises a proximal end part 5. The device 1 also comprises a protective sleeve 6. This protective sleeve 6 is able to slide with respect to the support sleeve 2 between a retracted standby configuration in which the needle 7 of the injection apparatus 4 is exposed, as shown in FIG. 6, and a deployed protective configuration in which the protective sleeve 6 covers the said needle 7 as shown in FIG. 9.

As shown in FIGS. 1 and 2, the device 1 comprises first retaining means for holding the protective sleeve 6 in its standby configuration in a first position, known as the injection position, these being in the form of two longitudinal bulges 8 formed on the internal surface 9 of the wall of the body 3 of the support sleeve 2 and of two first tabs 10 running axially in the proximal direction from the proximal end 11 of the protective sleeve 6. As a preference, the bulges 8 are diametrically opposed. Each bulge 8 comprises, at its proximal end, an internal retaining ramp 12 and each first tab 10 is equipped at its proximal end with a projection 13 the distal face of which is inclined and able to rest on the internal ramp 12 of the proximal end of the bulge 8 facing it. As will be explained later on, these first retaining means for retaining the protective sleeve 6 are able to be deactivated in order to cause the protective sleeve 6 to slide, in its retracted standby configuration, between a first position known as the injection position and a second position known as the end-of-injection position.

As shown in FIG. 2, the device 1 also comprises second retaining means for holding the protective sleeve 6 in its standby configuration in a second position, known as the end-of-injection position, these being in the form of a transverse retaining surface 14 situated at the proximal end of each bulge 8, facing the internal ramp 12 of the said bulge 8 and of two second tabs 15 running in the proximal direction from the proximal end 11 of the protective sleeve 6 along an axis slightly inclined with respect to the longitudinal axis of the injection apparatus 4, each second tab 15 being situated facing one said first tab 10, each second tab 15 being equipped at its proximal end with a hooked portion 16 the distal face 17 of which is able to rest on the transverse retaining surface 14 of the bulge 8 facing it. As will be explained later on, these second retaining means for retaining the protective sleeve 6 are able to be deactivated so as to allow the protective sleeve 6 to deploy at the end of injection.

As is apparent from FIGS. 1 to 3, the protective device 1 also comprises an intermediate collar 18 situated in the proximal end part 5 of the support sleeve 2. The proximal end part 5 of the support sleeve 2 comprises tabs 29, each tab 29 comprising a radial hooked portion 30 intended to retain the proximal face of the intermediate collar 18 in the proximal direction, the said radial hooked portion 30 comprising an internal ramp 31 the function of which will be explained later on. The intermediate collar 18 is able to slide with respect to the support sleeve 2 within the proximal end part 5 of this support sleeve 2. The intermediate collar 18 comprises collaboration means for collaborating with the piston head 19 of the injection apparatus 4. In the example depicted, these collaboration means are in the form of two diametrically opposed legs 20 running in the proximal direction, slightly offset from the body 21 of the collar 18 in the radial direction and connected to the proximal end of the collar 18 by radial bridges 22.

The intermediate collar 18 also comprises deactivation means for deactivating the first and second retaining means, these being in the form, in the example depicted, of a surface 23 projecting radially from the body 21 of the collar 18, this surface 23 being able to cooperate with the said first tabs 10 and the said second tabs 15 to deflect them circumferentially. In the example depicted, this surface 23 has an external ramp 24 facing each first tab 10 and a longitudinal recess 25 facing each second tab 15.

The protective device 1 also comprises at least one pushing means in the form, in the example depicted, of a spring 26 the proximal end of which bears against the distal end 27 of the intermediate collar 18 and the distal end of which bears against an annular rim 28 formed on the internal surface of the protective sleeve 6 at its proximal end 11.

In practice, the protective device 1 according to the invention is in the storage position as depicted in FIG. 4. The protective sleeve 6 has been inserted within the support sleeve 2 until the respective distal faces of the projections 13 of the first tabs 10 come into contact with the respective internal retaining ramps 12 of the bulges 8. Because they are slightly inclined with respect to the longitudinal axis of the device 1, the distal faces 17 of the hooked portions 16 of the second tab 15 are not in contact with the transverse surfaces 14 of the bulges 8. Then the spring 26 is inserted, its distal end bearing against the annular rim 28 of the protective sleeve 6. The intermediate collar 18 is then inserted by pressing on the internal ramps 31 of the radial hooked portions 30 of the tabs 29 which deflect as the said collar 18 passes. In the storage position, the intermediate collar 18 is therefore clipped into the proximal end part 5 of the support sleeve 2 by means of the tabs 29 and is retained in the proximal direction by the radial hooked portion 30 of these tabs 29. The proximal end of the spring 26 bears on the distal end 27 of the intermediate collar 18. The system is thus perfectly locked, with no risk of activation of the protective sleeve being triggered. In this position, the injection apparatus 4, in the form of a syringe in the example depicted, is assembled as shown in FIG. 5 and the product contained in the syringe can be injected.

At the end of injection, as shown in FIG. 6, the piston head 19 of the injection apparatus 4 comes into contact with the collaboration means, that is to say with the legs 20 in the example depicted, of the intermediate collar 18. By continuing to exert pressure and to push on the piston head 19, the intermediate collar 18 is moved in the distal direction and the external ramps 24 of the radially projecting surface 23 of the body 21 of the collar 18 deflect the first tabs 10 circumferentially. At the same time, the hooked portions 16 of the second tabs 15 are guided into the longitudinal recesses 25 of the radially projecting surface 23 of the body 21 of the intermediate collar 18 and the second tabs 15 are thus deflected circumferentially to come back parallel to the bulges 8.

Thus, the first retaining means for holding the protective sleeve 6 in its retracted standby configuration in the first, injection, position are deactivated and, under the pressure of the spring 26, the protective sleeve 6 is moved in the distal direction, over a short distance, until the distal faces 17 of the hooked portions 16 of the second tabs 15, guided by the longitudinal recesses 25, come into contact with the transverse retaining surfaces 14 of the bulges 8, as shown in FIG. 7. The protective sleeve 6 is then in its retracted standby configuration in the second, end-of-injection, position. In this position, the protective device 1 is immobilized. The piston is at the end of its travel and it is not possible to trigger activation of the protective sleeve 6 by continuing to push on the piston head 19.

To trigger activation of the protective sleeve, the user has to slightly release his pressure on the piston head 19. Thus, at this stage, the end-user may decide to activate the protective sleeve 6 while the needle 7 is still in the patient or may, on the other hand, decide to withdraw the needle 7 from the patient and then to activate the protective sleeve 6.

When the user slightly releases the pressure on the piston head 19, the intermediate collar 18 is moved in the proximal direction under the effect of the pushing of the spring 26. While this is happening, the surface 23 projecting radially from the body 21 of the collar 18 releases the second tabs 15 as shown in FIG. 8. These second tabs 15 return to their initial position slightly inclined with respect to the longitudinal axis of the device 1 and the distal faces 17 of the hooked portions 16 no longer bear against the transverse retaining surfaces 14 of the bulges 8.

Under the effect of the pushing of the spring 26, the protective sleeve 6 is then moved in the distal direction and covers the needle 7 (in chain line) as shown in FIG. 9.

It is evident from the foregoing that the invention provides decisive improvements to similar devices of the prior art by making it possible for the protective sleeve to be activated only at the end of injection and at the time when the end-user so decides.

It goes without saying that the invention is not restricted to the embodiment described hereinabove by way of example but that, on the contrary, it encompasses all alternative forms of embodiment that fall within the field of protection defined by the attached claims.

The invention claimed is:

1. A device for protecting an injection apparatus for injecting a product, the injection apparatus comprising a reservoir fitted with a needle at its distal end and a piston connected to an actuating rod surmounted by a piston head, the device comprising:
   a support sleeve comprising a body configured to accommodate the injection apparatus and a proximal end part;
   a protective sleeve configured to slide with respect to the support sleeve between a retracted standby configuration in which the needle is exposed and a deployed protective configuration in which the protective sleeve covers the needle;
   first retaining means arranged at the proximal end part of the support sleeve for holding the protective sleeve in a first position;
   second retaining means arranged at the proximal end part of the support sleeve for holding the protective sleeve in a second position, wherein the protective sleeve is appreciably offset in the distal direction with respect to the support sleeve;
   an intermediate collar situated at the proximal end part of the support sleeve, configured to slide with respect to the support sleeve within the proximal end part, the intermediate collar comprising means of collaboration with the piston head of the injection apparatus, and means of deactivating the first and second retaining means,
   the first retaining means configured to be deactivated by the deactivation means of the intermediate collar by pressure of the piston head in the distal direction on the collaboration means of the intermediate collar to cause the protective sleeve to slide in its retracted standby configuration between the first position and the second position; and
   the second retaining means configured to be deactivated by the deactivation means of the intermediate collar by release of the pressure of the piston head on the collaboration means of the intermediate collar to allow the protective sleeve to deploy under the action of pushing means.

2. The device according to claim 1, wherein the means of collaboration of the intermediate collar with the piston head comprises two diametrically opposed legs running in the proximal direction, slightly offset from the body of the collar in the radial direction and connected to the proximal end of the collar by radial bridges.

3. The device according to claim 1 wherein the first retaining means comprises two diametrically opposed longitudinal bulges formed on the internal surface of the wall of the body of the support sleeve, each bulge at its proximal end comprising an internal retaining ramp and two first tabs running axially in the proximal direction from the proximal end of the protective sleeve, each of the said first tabs being provided at its proximal end with a projection the distal face of which is inclined and able to rest on the internal ramp of the proximal end of one of said bulges.

4. The device according to claim 3, wherein the second retaining means comprises a transverse retaining surface situated at the proximal end of each bulge facing the internal ramp of the bulge and two second tabs running in the proximal direction from the proximal end of the protective sleeve along an axis slightly inclined with respect to the longitudinal axis of the injection apparatus, each second tab being situated facing one said first tab, each second tab being equipped at its proximal end with a hooked portion the distal face of which is able to rest against the transverse retaining surface of the bulge facing it.

5. The device according to claim 4, wherein the deactivation means for deactivating the first and second retaining means are a surface projecting radially from the body of the collar, the surface configured to collaborate with the first tabs and with the second tabs to deflect them circumferentially.

6. The device according to claim 5 wherein the pushing means are a spring, the proximal end of which bears against the distal end of the intermediate collar and the distal end of which bears against an annular rim formed on the internal surface of the protective sleeve at its proximal end.

* * * * *